United States Patent
Faccioli et al.

[19]

[11] Patent Number: 5,881,878
[45] Date of Patent: Mar. 16, 1999

[54] MULTIPURPOSE CONTAINER IN PARTICULAR FOR THREADED WIRES FOR OPERATIONS IN ORTHOPAEDIC SURGERY

[75] Inventors: Giovanni Faccioli, Monzambano; Daniele Venturini, Povegliano., both of Italy; Dietmar Pennig, Cologne, Germany

[73] Assignee: Orthofix S.r.l., Italy

[21] Appl. No.: 973,572

[22] PCT Filed: Feb. 24, 1996

[86] PCT No.: PCT/EP96/00768

§ 371 Date: Dec. 5, 1997

§ 102(e) Date: Dec. 5, 1997

[87] PCT Pub. No.: WO96/39091

PCT Pub. Date: Dec. 12, 1996

[30] Foreign Application Priority Data

Jun. 6, 1995 [IT] Italy ................................ VR95A0052

[51] Int. Cl.⁶ ..................................................... A61B 19/02
[52] U.S. Cl. .......................... 206/438; 206/370; 206/339; 206/443; 206/459.5
[58] Field of Search .................................... 206/305, 339, 206/363, 63.3, 438, 443, 459.5, 504, 370, 372, 373; 220/23.4

[56] References Cited

U.S. PATENT DOCUMENTS

| | | |
|---|---|---|
| 2,267,008 | 12/1941 | Zimmer . |
| 3,138,263 | 6/1964 | Brass . |
| 4,932,533 | 6/1990 | Collier ..................................... 206/370 |
| 5,150,788 | 9/1992 | Weissman ................................ 206/370 |
| 5,267,668 | 12/1993 | Jones ........................................ 206/363 |
| 5,291,997 | 3/1994 | He et al. .................................. 206/370 |
| 5,358,112 | 10/1994 | Gardner ................................... 206/443 |
| 5,372,252 | 12/1994 | Alexander ............................... 206/370 |
| 5,615,770 | 4/1997 | Applebaum et al. .................... 206/438 |
| 5,669,501 | 9/1997 | Hissong et al. .......................... 206/363 |

FOREIGN PATENT DOCUMENTS

| | | |
|---|---|---|
| 1005149 | 5/1993 | Belgium . |
| 561780 | 10/1923 | France . |
| 2659224 | 9/1991 | France . |
| 9101408 | 7/1992 | Germany . |
| 4406374 | 9/1994 | Germany . |
| 692103 | 5/1993 | United Kingdom . |
| WO9406478 | 3/1994 | WIPO . |

*Primary Examiner*—Paul T. Sewell
*Assistant Examiner*—Luan K. Bui
*Attorney, Agent, or Firm*—Hopgood, Calimafde, Kalil & Judlowe

[57] ABSTRACT

A multipurpose container, particularly for threaded wires for bone surgery operations, comprising: a substantially rectangular base (2), a central body (3), which is removably secured to the said base (2) by securing means (16), suitable for containing a plurality of threaded wire (6), which is shorter in height than the said wires, so that the ends (7) thereof project above in order that they may be selected by an operator, a lid (4) secured to the said body (3), capable of covering the projecting ends (7) of the wires when the lid (4) is placed in the closed position, in which the said body (3) is subdivided into a plurality of separate spaces (9), which are accessible from the upper part (3') of the said body (3), each of which is capable of containing a plurality of threaded wires (6) of the same size and having threaded parts (8) of identical length and diameter.

17 Claims, 4 Drawing Sheets

MULTIPURPOSE CONTAINER IN PARTICULAR FOR THREADED WIRES FOR OPERATIONS IN ORTHOPAEDIC SURGERY

BACKGROUND OF THE INVENTION

This invention relates to a multipurpose container which is particularly suitable for containing "threaded wires" and corresponding washers, of different sizes and characteristics, of the type used in orthopaedic surgery.

As is known from German patent application No. P 4309707, threaded wires are an improvement on the Kirschner wires used in orthopaedic surgery to secure bone fragments to the main bone or to reconstruct broken small bones. The threaded wires are not completely smooth (like the Kirschner wires), but their ends which penetrate the bone are threaded with a thread diameter which is less than the diameter of the remaining cylindrical shank of the wire, so as to form a step at the point where the threaded part joins the smooth part. This step serves to apply a compression force against the bone fragment towards the part of the bone from which the said fragment has become detached, when the threaded wire is screwed up. In some cases the thrust surface provided by this step is not sufficient, or the pressure exerted locally on the fragment is too high and might damage it. In these circumstances the use of special washers is provided for, the threaded part is threaded through them and they come up against the said step they enlarge the area on the said fragment supporting the threaded wire.

Threaded wires of different diameter and different wire diameters are used according to the characteristics and size of the bone fragments and the bones from which the fragments have become detached, for example wires with a diameter of $\phi$ 1.5 mm, 2.0 mm or 3.0 mm, with corresponding thread diameters $\phi$ 1.2 mm, 1.6 mm or 2.2 mm, and different lengths of the threaded part, for example 7 mm, 9 mm, 11 mm, 13 mm, 15 mm, 17 mm, 19 mm and 21 mm for wires with threads of diameter $\phi$ 1.2; 11 mm, 13 mm, 15 mm, 17 mm, 19 mm, 21 mm, 23 mm, 25 mm, 30 mm, 35 mm, 40 mm and 45 mm for wires with threads of $\phi$ 1.6; and 20 mm, 25 mm, 30 mm, 35 mm, 40 mm, 45 mm, 50 mm and 55 mm for wires with threads of $\phi$ 2.2.

Containers for bone bolts or bolts which separate bolts or bolts of different diameters and lengths are known, but these containers have the following disadvantage. If bolts or bolts of a different size than that for the specified position in the container are placed in it in error, the surgeon or the personnel responsible for passing tools to the surgeon may be misled and therefore use a bolt/screw which is slightly different from that required, or, if the differences are clearly visible, be forced to put the incorrect bolt/screw back in the container and take another, in the hope that the second will be the desired one. In the special case of threaded wires, in addition to having different diameters, they also have a wide range of lengths of the threaded portion which often differ from each other by only one or two millimeters. Obviously it would be very useful for the surgeon or the personnel responsible for passing tools to the surgeon to check the size of the threaded wire immediately and thus to be sure of the size of threaded wire which they have in their hands.

GB-A-O-692 103 discloses a multipurpose container with a substantially rectangular base, a central body removably secured to said base and a lid, whereby the body is subdivided into a plurality of separate spaces. This container is suitable for containing a plurality of threaded wires so that the ends thereof project above the body and its lid is capable of covering the projecting ends of the threaded wires.

BRIEF STATEMENT OF THE INVENTION

The main object or this invention is to provide orthopaedic surgeons or the personnel responsible for passing tools to the surgeon with a container which keeps threaded wires separate according to the different diameters and the different lengths of the threaded part of each wire, and which can be used to make an easy check on these dimensions at the time of use.

The invention is also designed to provide a container which can also hold washers of different diameters which may be used with the said threaded wires, and which also makes it easy to select washers by directly using the same threaded wire with which they can be used, without having to touch them with the hands.

Another object of this invention is to provide a multiple container comprising a plurality of similar or identical elements which can easily be assembled together, each element being designed to contain threaded wires of the same diameter, but different lengths of the threaded part, and the corresponding washers.

A further object of this invention is to provide a container capable of holding at least four identical threaded wires of each diameter and each length of the threaded part. In this way it is possible to have a sufficient stock of each threaded wire during any surgery. Stocks may also be restored easily after surgery and before the next use of the container in a successive operation.

According to the present invention, there is provided a multipurpose container, particularly for threaded wires for bone surgery operations, comprising:

a substantially plate-like rectangular base;

a central body which is removably secured to the said base by removable securing means, said central body having a plurality of spaces suitable for housing a plurality of threaded wires so that the ends thereof project above the top surface of said body in order that they may be selected by an operator;

a lid capable of covering the projecting ends of the wires when the lid is in its closed position;

characterized in that:

said central body is a substantially prismatic body with a top surface and a bottom surface which are substantially parallel to each other, and with four lateral surfaces which are substantially perpendicular to said top surface;

all of said spaces being cylindrical through cavities formed in said central body extending from said top surface in a direction substantially perpendicular thereto, each of said cylindrical cavities having a diameter sufficient to house a plurality of wires of identical diameter, said top surface having alongside each of said cylindrical cavities an indication of the length of the threaded part of the wires to be housed therein; and means being provided for measuring the length of the threaded part of a wire.

The said multipurpose container is also characterized in that between the said base and the bottom of the said central body there is a member capable of preserving the points of the wires from harm and avoiding contamination of these parts with non-biocompatible materials, and in that the said central body is provided with means for measuring the length of the threaded part of a threaded wire.

A first advantage offered by the proposed arrangement lies in the fact that the operator, who must take a threaded wire of a specific diameter having a threaded portion of specific length, is immediately guided by external indications to select the wire from the container space containing only wires of the same diameter. When the operator has any doubt whether the threaded wire does not have the desired length of thread, he can measure that length immediately. This measurement is checked by placing the threaded wire in a channel provided with a metric scale constructed on an easily accessible part of the container itself, to provide an immediate and simple measurement of the length of the threaded part of the threaded wire.

A second advantage lies in the fact that when it is necessary to add a washer to the threaded wire in order to increase its support surface on the bone fragment to which it has to be applied, this operation is particularly easy and ensures that the washer is not touched with the hands. In fact the washers are arranged in a stack alongside each other in a vertical groove made in the container itself and provided with a suitable access slot to it. It is therefore possible by grasping a threaded wire by its non-threaded portion to thread a washer around it easily by introducing the threaded part of the said wire through the said slot into the hole in the washer which can be seen through the said slot providing access to the vertical groove, and remove the washer merely by lifting the threaded wire vertically with its washer which is by then in its position of use.

Another advantage is provided by the fact that the points of the threaded portions of the said wires are kept in contact with an elastic-plastic biocompatible material. In this way the points of the threaded wires are not damaged while the container is being filled or transported, and at the same time if any dust which is detached from the base supporting the points remains on the wire during the operations described above or during washing and sterilization, and therefore comes into contact with the bone, this biocompatible material will not cause any infection in the bone itself.

A further advantage is provided by the fact that the container comprises several members which can be assembled together to form the container itself. In this way, in those cases where the high level of specialization of the surgeon requires it, only the members designed to contain threaded wires and the corresponding washers of small and medium diameter can be assembled, for example in the case of surgeons specializing in the hand, or in small bones, or only members designed to contain threaded wires and their corresponding washers of small and large diameter, for example in the case of surgeons specializing in the long bones (tibia, femur, etc.).

Finally a further advantage is provided by the fact that the container cannot be opened accidentally during handling, for example in transport from the store to the operating theater, as it is provided with a lid which requires an upwardly exerted pressure in order to open it. In this way protected transport of the threaded wires from the place of sterilization to the operating theater is ensured.

BRIEF DESCRIPTION OF THE DRAWINGS

Other advantages will appear from the following detailed description in which some possible embodiments of this invention are illustrated, with non-restrictive effect, with reference to the appended drawings in which.

DETAILED DESCRIPTION

Figure 1:
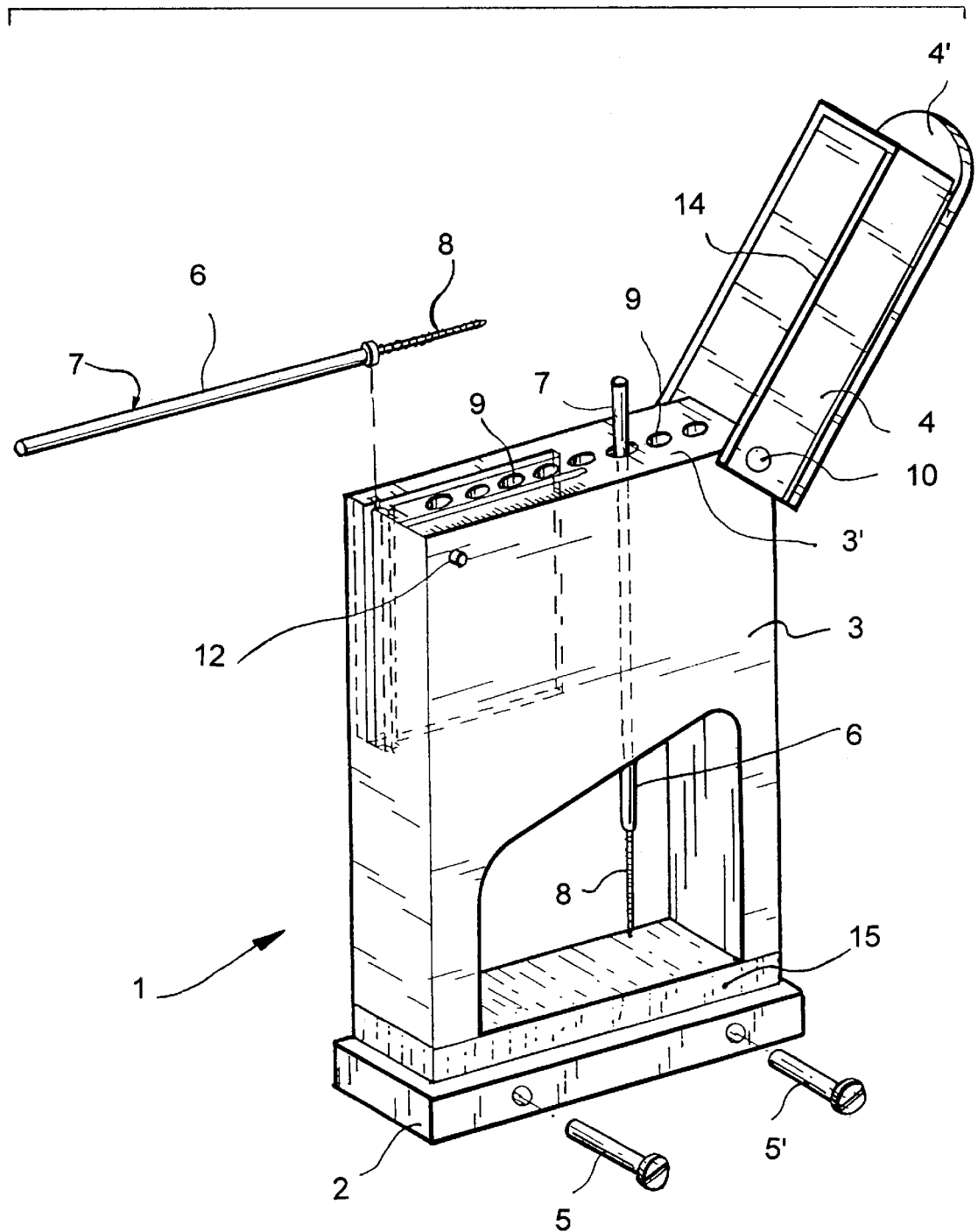
FIG. 1 is an axonometric view of a first embodiment of a container for threaded wires according to this invention, and a threaded wire onto which a washer taken from the container itself has just been threaded.

With reference to the figures listed above, it will be noted that the container according to the invention, indicated as a whole by reference number 1, comprises: a base 2 comprising a substantially rectangular metal plate, a central body 3, removably secured to base 2 by fixing means which are not illustrated, and a lid 4 secured to said body 3.

Said central body 3 is capable of containing a plurality of threaded wires 6, only one of which is illustrated, and is shorter in height than the said wires 6 so that the ends 7 thereof project above it. Said body 3 is subdivided into a plurality of separate spaces 9, preferably comprising cylindrical cavities with a vertical longitudinal axis, which are accessible from the top 3' of said body 3, and each capable of containing at least 4 threaded wires 6 of the same size and having threaded parts 8 of the same length and diameter. In this way an operator, that is an orthopaedic surgeon or a person responsible for passing tools to an orthopaedic surgeon, can easily select a wire 6 by grasping it by its non-threaded end 7.

The container therefor provides a number of spaces 9 housing wires 6 corresponding to the number of different wires envisaged for the said container. The length of the said threaded part 8, expressed in millimeters, is then shown against each space 9 so as to aid selection of wire 6 by the operator.

In order to aid cleaning and sterilization, spaces 9 have the shape of cylindrical chambers and have dimensions such that at least four threaded wires of the same diameter and having the same length of the threaded part 8 of wire 6 can be placed in them.

The said lid 4 is secured to said central body 3 by means of two hinges 10 and 10' having substantially horizontal axes located in the vicinity of an upper corner 11 of said central body 3, on the posterior side with respect to the person who has to open the container, thus ensuring that lid 4 rotates in a vertical plane.

Said lid 4 and said central body 3 are provided with pressure locking means 12 which act together to hold the lid in the closed position. The said locking means comprise a sphere acting together with a cylindrical cavity having a horizontal longitudinal axis and a diameter slightly less than that of the sphere, located one on said central body 3 and the other on said lid 4 respectively. The sphere is located within a seat provided in one of the side walls 13 of said central body 3, near the upper front edge thereof, slightly projecting from the plane of the corresponding side walls 13 and capable of elastic displacement along an axis perpendicular to the said walls, so that when container 1 is closed the said sphere can be caused to reenter its seat when corner 14 of the lid comes into contact with the sphere itself and can therefore return to its own position when the corresponding longitudinal axis of the cylindrical cavity is in line with the horizontal axis passing through the center of the sphere.

Obviously said locking means 12 may be replaced by other equivalent means which provide a releasable lock between the lid and the central body.

Figure 2:
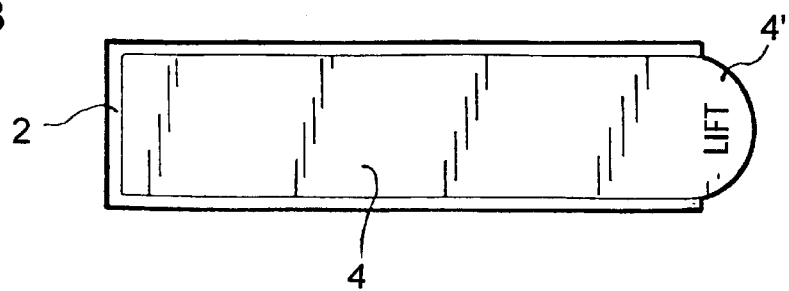
FIG. 2 is a view from above of the container in the preceding figure with the lid in the closed position.

As illustrated in FIG. 2, lid 4 also has a forwardly projecting tab 4' capable of allowing the operator to exert an upward pressure to raise lid 4 when the container is opened.

In addition to this, the lid is shaped in such a way that it can cover the said projecting ends of the wires when the lid is placed in the closed position.

Between said base 2 and the bottom of said central body 3 of container 1, there is a member 15 which preserves the points of wires 6 from harm when these are placed in container 1 and while the container filled with the said wires is transported. Said member 15 also has the task of avoiding contamination of the wires by non-biocompatible materials, which if they were detached from the base through the cutting effect of the points of the wires could stick to the thread and therefore be introduced with this into the bone receiving treatment.

Figure 3:
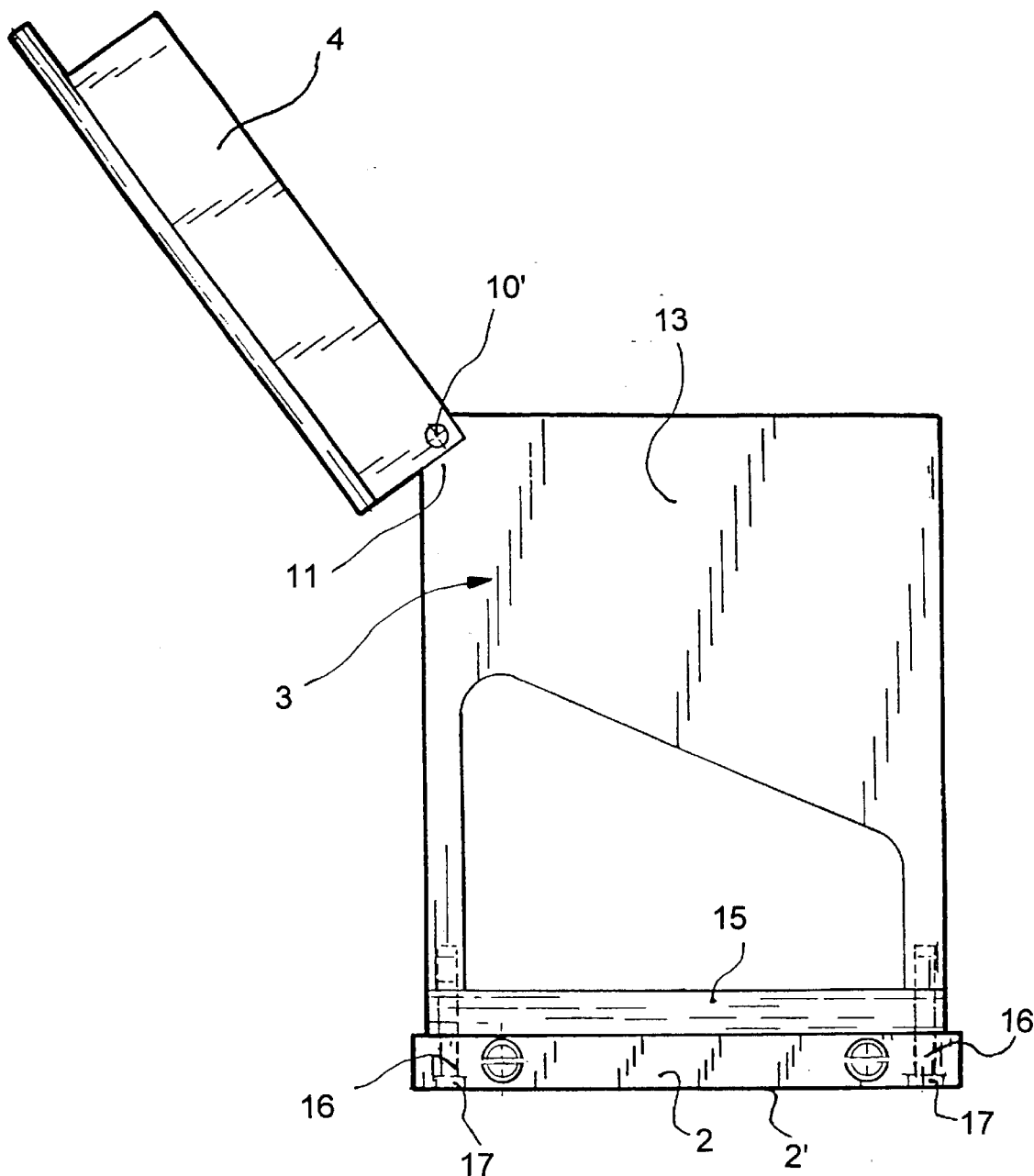
FIG. 3 is a side view of the container in FIG. 1 with the lid in the open position.

In a preferred embodiment said member 15 comprises a layer of biocompatible elastic-plastic material placed between the said supporting base and the bottom surface of the said central body. In particular, in the embodiment illustrated in FIG. 3, the said member comprises a rectangular prism of biocompatible elastic-plastic material, such a PSU polysulphone, the dimensions of which in plan correspond to those of central body 3, but are smaller than those of said base 2.

The said layer of biocompatible elastic-plastic material is secured to body 3 and the base of support 2 by securing means 16 comprising a pair of bolts, the heads 17 of which are housed in cavities located in bottom surface 2' of the said base and the shanks of which can be screwed into central body 3 through two holes passing through the member of biocompatible material.

Figure 4:
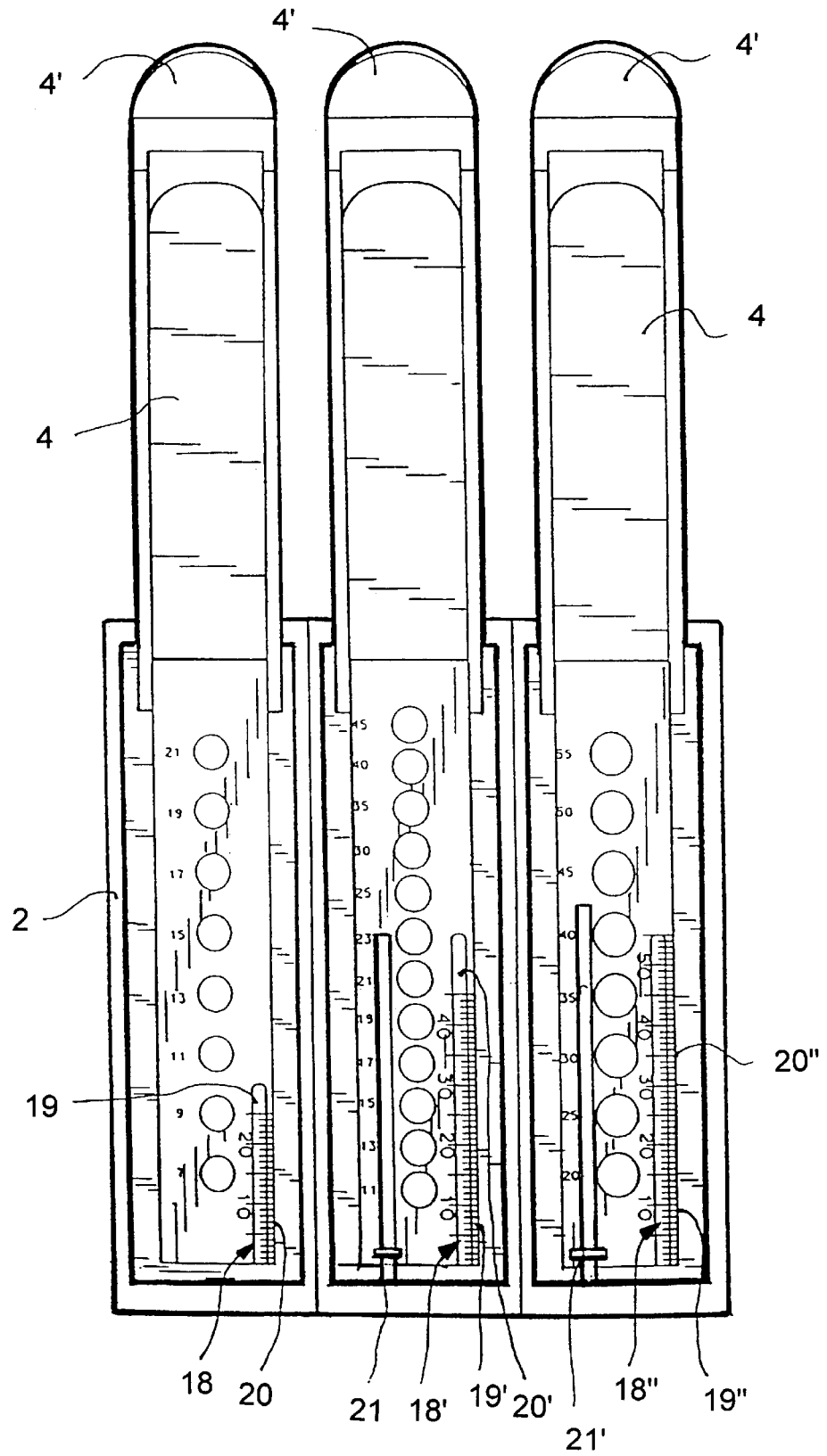
FIG. 4 is a view from above of three similar containers according to this invention for threaded wires of small, medium and large diameters associated together and with the lid in the open position.

FIG. 4 illustrates three similar containers, for threaded wires of small, medium and large diameter respectively, associated together to form a single multiple container. The three containers are joined together by screw means, not illustrated, comprising, e.g., two bolts and two securing nuts. Each supporting base has two through transverse holes into which the bolts are passed. The nuts on the other hand are housed in cavities located in the outer side wall of the container base, on the side opposite the both heads.

FIG. 4 also shows means 18, 18' and 18" for measuring the length of the threaded part of a threaded wire. The said measuring means comprise a groove 19, 19' and 19" provided on the upper surface of said central body 3, provided with a scale 20, 20' and 20" graduated in millimeters, of a length equal to at least the length of the longest threaded part of the wires contained in the container.

It is obvious that said measurement means 18 can be provided not only on the said upper surface of body 3, in a position different from that indicated in FIG. 4, but also on any other outer surface of the container.

Figure 5:
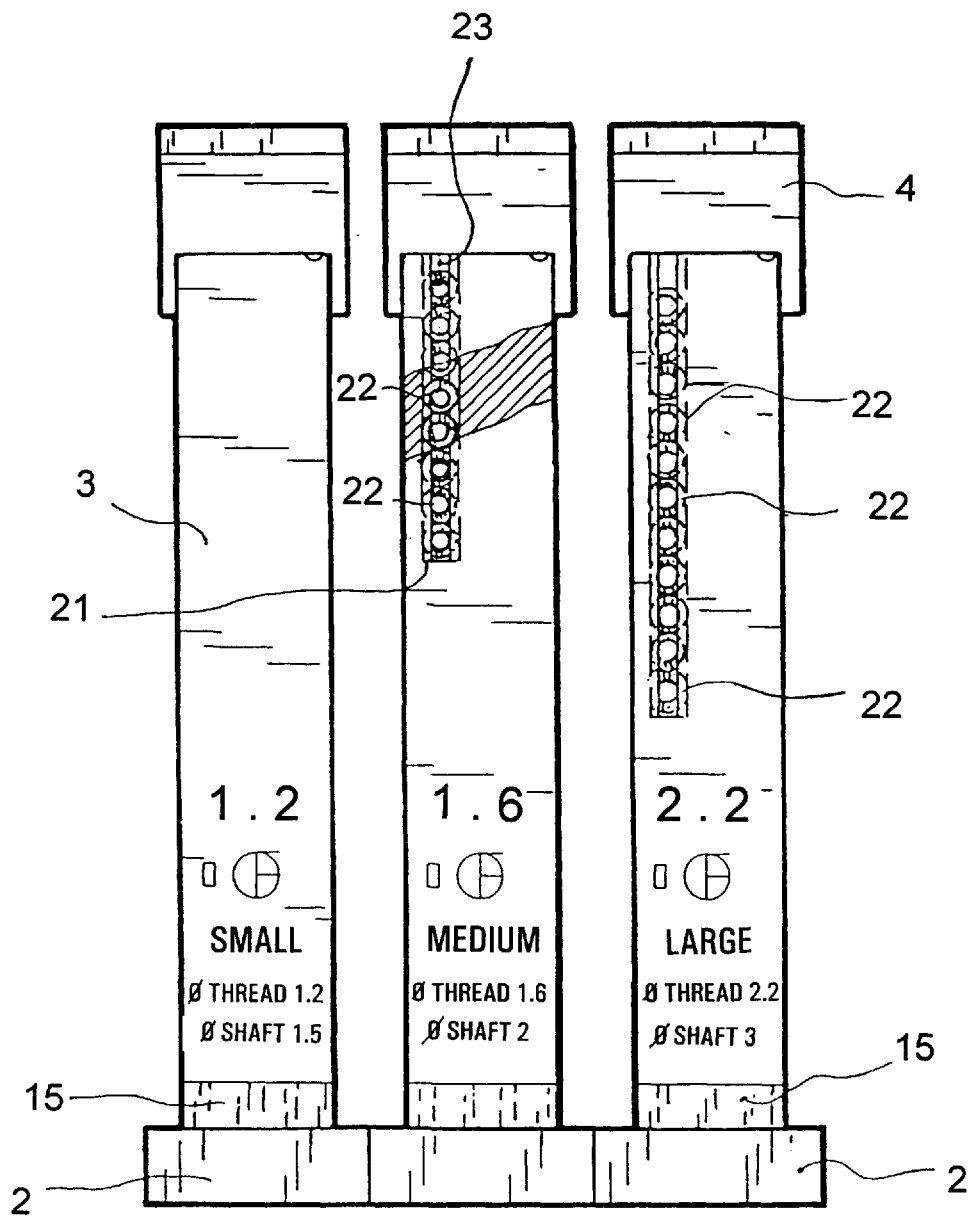
FIG. 5 is a front view of the three containers in the foregoing figure in which one is in partial cross-section.

FIGS. 4 and 5 clearly show that containers according to this invention may also be provided with a magazine 21, 21' for housing a plurality of washers 22, 22' which can be used in combination with the said threaded wires. The washers are taken directly from the container, using the threaded wire with which they will be subsequently used, as illustrated in FIG. 1.

The said magazine 21, 21' comprises a vertical channel made in central body 3 of container 1, the transverse cross-section of which is slightly greater than the diameter of washers 22 so that they can be stacked vertically. The said channel is accessible from the exterior through a vertical slot 23 which extends along the middle of the channel for insertion of the threaded end of a wire. The said slot extends inwards in a direction perpendicular to the plane of the channel to allow an operator to insert the threaded part of a wire into the hole of the washer selected. After the washer has been threaded on, the operator lifts the wire vertically together with the washer to remove it from its housing.

Containers for wires of large diameter do not need washers to increase their supporting base on the bone and therefore, as illustrated in FIG. 5, the corresponding container does not provide a magazine for washers.

It is also obvious that a plurality of containers of different or identical characteristics, or for wires of different or the same diameters, can be assembled together into a single piece using a base consisting of a rectangular plate, instead of assembling the individual rectangular bases of various containers, through the use of threaded means of attachment.

What is claimed is:

1. A multipurpose container, particularly for threaded wires for bone surgery operations, comprising:

a substantially plate-like rectangular base (2);

a central body (3) which is removably secured to the said base (2) by removable securing means (16), said central body (3) having a plurality of spaces (9) suitable for housing a plurality of threaded wires (6), so that the ends (7) thereof project above a top surface (3') of said body (3) in order that they may be selected by an operator;

a lid (4) capable of covering the projecting ends (7) of the wires when the lid (4) is in its closed position;

characterized in that:

said central body (3) is a substantially prismatic body with the top surface (3') and the bottom surface which are substantially parallel to each other, and with four lateral surfaces which are substantially perpendicular to said top surface (3');

all of said spaces (9) being cylindrical through cavities formed in said central body (3) extending from said top surface (3') in a direction substantially perpendicular thereto, each of said cylindrical cavities (9) having a diameter sufficient to house a plurality of wires of identical diameter, said top surface (3') having alongside each of said cylindrical cavities (9) an indication of the length of the threaded part of the wires to be housed therein; and means (18, 18', 18") being provided for measuring the length of the threaded part of a wire.

2. A multipurpose container according to claim 1, characterized in that a member (15) to keep the points of the wires (6) safe from harm and to avoid contamination by non-biocompatible materials is placed between the said base (2) and the lower part of said central body (3).

3. A multipurpose container according to claim 1, characterized in that the said measurement means (18, 18', 18") comprise a channel made in an outer surface of the said central body (3) provided with a scale (19, 19', 19") graduated in millimeters, of a length which is at least equal to the length of the longest threaded part (8) of the wires (6) held in the container.

4. A multipurpose container according to claim 2, characterized in that the said measurement means (18, 18', 18") comprise a channel made in an outer surface of the said central body (3) provided with a scale (19, 19', 19") graduated in millimeters, of a length which is at least equal to the length of the longest threaded part (8) of the wires (6) held in the container.

5. A multipurpose container according to claim 2, in which the said member (15) comprises a layer of biocompatible elastic-plastic material placed between the said supporting base (2) and the bottom surface of the said central body (3).

6. A multipurpose container according to claim 5, in which the said layer has dimensions in plan corresponding to those of the said central body (3), but smaller than those of the said supporting base (2), and is secured thereto by means of securing means (16).

7. A multipurpose container according to claim 6, characterized in that the said securing means (16) comprise a pair of bolts whose heads are housed within cavities (17) located on the lower surface (2') of the said base (2) and whose shanks can be screwed into the said central body (3) through two holes passing through the member (15) of biocompatible material.

8. A multipurpose container according to claim 1, characterized in that the said lid (4) is secured to the said central body by hinge means (10, 10') which have a substantially horizontal axis located in the vicinity of an upper corner (11) of the said central body (3) in such a way as to permit rotation of the lid (4) in a vertical plane.

9. A multipurpose container according to claim 8, in which the said lid (4) and the said central body (3) are provided with pressure locking means (12) which act together in order to hold the lid in the closed position, and in which the said lid (4) has a forwardly projecting tab (4') to permit the operator to exert an upward pressure in order to raise the lid.

10. A multipurpose container according to claim 9, characterized in that the locking means (12) are of the sphere type, elastically supported in one of the said lid (4) and central body (3) which can snap into an opposing shaped seat formed in the other of the said lid (4) and central body (3).

11. A multipurpose container according to claim 1, characterized in that a magazine (21) is provided for housing a plurality of washers (22) which can be used in combination with the said threaded wires (6), in which the said washers (22) are taken directly from the container using the said threaded wire (6) with which they will then be used.

12. A multipurpose container according to claim 11, characterized in that the said magazine (21) comprises a vertical channel made in the central body (3) of the container with a transverse cross-section which is slightly greater in size than the diameter of the washers (22), in such a way that the latter can be stacked vertically, the said channel being accessible from the exterior through a vertical slot (23) which extends along the middle of the channel for insertion of the threaded end of a wire (6).

13. A multipurpose container according to claim 11, characterized in that the said slot (23) is extended inwards in a direction perpendicular to the plane of the channel to allow the threaded part (8) of a wire (6) to be inserted when a washer (22) is selected.

14. A multipurpose container according to claim 1, characterized in that the said spaces (9) are of a size such that at least four identical threaded wires for each diameter and length of the threaded part (8) can be housed within.

15. A multipurpose container according to claim 1, preceding claim, characterized in that means of attachment (5, 5') to other similar adjacent containers are provided.

16. A multipurpose container according to claim 15, characterized in that the said securing means (5, 5') comprise bolt means which are capable of removably connecting the base (2) of a container to one or more bases (2) of another adjacent container.

17. A multipurpose container according to claim 16, in which the said base comprises a metal plate which is capable of removably anchoring a plurality of central bodies (3).

* * * * *